United States Patent
Delesalle et al.

(10) Patent No.: US 6,803,497 B1
(45) Date of Patent: Oct. 12, 2004

(54) **METHODS OF MAKING CYTOPLASMIC MALE STERILE CHICORY PLANTS COMPRISING THE ORF 522 OF *HELIANTHUS ANNUUS***

(75) Inventors: Louis Delesalle, Cappelle en Pevelle (FR); Charles Dhellemmes, Cappelle en Pevelle (FR); Michel Desprez, Cappelle en Pevelle (FR)

(73) Assignee: Florimond Desprez Veuve et Fils, Cappelle en Pevelle (FR)

( * ) Notice: Subject to any disclaimer, the term of this patent is extended or adjusted under 35 U.S.C. 154(b) by 0 days.

(21) Appl. No.: 09/194,598

(22) PCT Filed: May 30, 1997

(86) PCT No.: PCT/FR97/00944

§ 371 (c)(1),
(2), (4) Date: Nov. 30, 1998

(87) PCT Pub. No.: WO97/45548

PCT Pub. Date: Dec. 4, 1997

(30) Foreign Application Priority Data

May 31, 1996 (FR) .............................. 96 06725

(51) Int. Cl.⁷ ............................ A01H 1/00; A01H 1/02; A01H 1/04; A01H 4/00
(52) U.S. Cl. ....................... 800/266; 435/430; 800/268; 800/269; 800/274
(58) Field of Search ................................ 800/274, 277, 800/298, 303, 304, 322

(56) References Cited

U.S. PATENT DOCUMENTS 5,914,447 A  *  6/1999  Araya et al. ................. 800/274
6,066,779 A  *  5/2000  Yan ............................ 800/274

FOREIGN PATENT DOCUMENTS

EP   0 771 523 A1   5/1997
GB   2 211 305 A    6/1989

OTHER PUBLICATIONS

Reeck et al 1987, Cell 50:667.*
Dubreucq et al 1999, Theoretical and Applied Genetics 99:1094–1105.*
Laver et al. The Plant Journal. vol. 1, pp. 185–193, 1991.*
Rambaud et al. Theoretical and Applied Genetics. vol. 87, pp. 347–352, 1993.*
Rambaud et al. Comptes Rendus de l'Academie d'Aggriculture de France. vol. 80, pp. 63–67. (Only Abstract in English), 1994.*
Koehler et al., Cytoplasmic male sterility in sunflower is correlated with the co–transription of a new open reading frame with the atpA gene, vol. 227, No. 3, (1991), pp 369–376, XP000608949.
Rambaud et al., Chicory–sunflower protoplast fusion, Comptes Rendus De L'Academie D'Argriculture De France, vol. 80, No. 7, (1994), pp 63–67, XP000197041. Abstract only.
Rambaud et al., Male–sterile chicory cybirds obtained by intergeneric protoplast fusion, vol. 87, No. 3, (1993), pp 347–352, XP000197036.

* cited by examiner

*Primary Examiner*—David H Kruse
(74) *Attorney, Agent, or Firm*—Foley & Lardner LLP

(57) ABSTRACT

The invention is directed to methods of making cytoplasmic male sterile chicory plants by identifying a diagnostic 347 bp fragment of the orf 522 of *Helianthus annuus*.

10 Claims, No Drawings

METHODS OF MAKING CYTOPLASMIC MALE STERILE CHICORY PLANTS COMPRISING THE ORF 522 OF *HELIANTHUS ANNUUS*

The present invention relates to the use of nucleotide sequences which allows cytoplasmic-type male sterility to be imparted to plants of the genus Cichorium.

The genus Cichorium includes plants which are of great interest in the agrifood industry, such as the various types of chicory and endives.

These are plants which have male and female reproduction systems at the same time and are therefore capable of self-fertilization. Such an event is undesirable when it is desired to carry out crosses with a plant of another variety in order to obtain hybrids.

In *Cichorium intybus*, plants which exhibit nuclear male sterility have already been proposed. However, cytoplasmic male sterility is an interesting solution for the production of hybrid species.

Cytoplasmic male sterility is a characteristic that is transmitted by the female parent of a plant (maternal inheritance) and which prevents the formation of viable pollen. Good-quality male sterility must not affect female fertility of the plant to allow it to be crossed with male fertile plants. It is therefore desirable to have available a system which imparts such stable cytoplasmic male sterility.

It is also desirable to have available a reliable marker of this cytoplasmic male sterility which allows plant cells to be selected even before the development of a complete plant which exhibits all of the phenotypic characteristics.

The present invention therefore relates to a recombinant plant genome, characterized in that it comprises specific chicory genes and a nucleotide sequence conferring male sterility, which is borne by the sunflower orf 522 sequence or by a sequence with at least 50%, advantageously at least 90%, homology with the said orf 522 sequence.

The orf 522 sequence is a sequence which was revealed in sunflower (Helianthus), in particular *H. annuus*, where it seems to be associated with cytoplasmic male sterility (Köhler et al, Mol. Gen. Genet., 1991, 227: 369–376).

The applicant has found that the presence of this orf 522 sequence in the genome of a plant of the genus Cichorium was linked to cytoplasmic male sterility.

Sequences which are suitable for carrying out the invention comprise sequences borne by the above-described orf 522 sequence, as well as by sequences with a similarity of at least 50%, preferably at least 80%. Suitable sequences advantageously show a similarity of 90% with the said orf 522 sequence, and comprise in particular the sequences which encode the same protein, taking into consideration the degeneration of the genetic code, or a protein in which certain amino acids were replaced by equivalent amino acids. The term "Equivalent amino acids" is understood to mean amino acids which have similar chemical behavior and/or similar molecular weights. They also comprise sequences which encode a protein in which one or more amino acids which are not essential for the activity have been deleted or replaced.

The genome can be of the nuclear or mitochondrial type.

When the sequence is present in the nuclear genome, the latter will also comprise a pre-sequence which allows the Translation product of this sequence to enter the mitochondria.

The recombinant genome is preferably a mitochondrial genome. The invention therefore also relates to a mitochondrion which comprises a recombinant genome as defined above.

In particular, the invention relates to a mitochondrion, characterized in that it comprises at least one nucleotide fragment of 347 bp which is borne by the orf 522 sequence or a sequence with at least 90% homology with the said fragment.

Within the orf 522 sequence (Köhler et al, Mol. Gen. Genet 1991), the 347 bp sequence is flanked by primers of the sequences:

SEQ ID NO 1: 5'CCCCCTCCCTGGTGGATCCGGCG3'
SEQ ID NO 2: 5'CCCTCTATGAGTACCGTTCTCTCACG3'

The invention relates to a recombinant plant cytoplasm, characterized in that it comprises a nucleus comprising the genome of the genus Cichorium and a recombinant genome defined hereinabove, in particular a cytoplasm which comprises mitochondria comprising a nucleotide sequence borne by the *Helianthus annuus* orf 522 sequence or by a sequence with at least 50% homology.

The recombinant plant cells comprising such a cytoplasm are within the scope of the invention, in particular a plant cell which comprises a nucleus comprising essentially the genome of a species selected from amongst *Cichorium intybus* and *Cichorium endivia*.

Without limiting the invention in any way, the following cultivation groups may be mentioned amongst these species:

| | |
|---|---|
| *Cichorium intybys* L: | "wild improved" chicories |
| | "Barbe de Capucin" chicories |
| | "sugar loaf" chicories |
| | "Chioggia" chicories |
| | "Verona" chicories |
| | "Catalonia" chicories |
| | "Treviso" chicories |
| | "Variegato di Castelfranco" chicories |
| | "Witloof" chicories (or |
| | "Brussels" chicory or |
| | "chicon" chicory) |
| | "Soncino" chicories |
| "Industrial" chicories (for roasting and for sugars) | |
| | "fodder" or "game" |
| | chicories . . . |
| *Cichorium endivia* L.: | "Scarole" endives |
| | "frisée" endives . . . |

These are so-called large-rooted chicories (industrial, fodder and Witloof) or so-called salad chicories (green, red, variegated, for forcing or not).

The expert will be able to apply the invention without difficulty, in particular by referring to "Génétique et Amélioration de la Chicorée industrielle" [Genetics and Improvement of Industrial Chicory], DESPREZ et al., specialist meeting on Nov. 30, 1994, at the Académie d'Agriculture de France, No. 80 (7) 48–49.

According to another aspect the invention relates to a method of producing a plant of the chicory genus or of the reproduction material of this plant which exhibits cytoplasmic male sterility, characterized in that a nucleotide sequence borne by the sunflower orf 522 sequence or by a sequence with at least 50%, preferably at least 90%, homology with the said orf 522 sequence, is integrated into the cell genome of this plant. The scope of the invention extends to the plant (or the production material), with the exception of plant varieties.

It also relates to an essentially non-biological method of preparing plant hybrids, characterized in that a plant which can be obtained by the above-described method is crossed with a plant of the same species which lacks the Helianthus annuus orf 522 sequence or a sequence which has at least 90% homology with the said orf 522 sequence.

In another aspect the invention relates to a method of selecting cytoplasmic male sterility in a plant of the genus Cichorium, characterized in that the mitochondrial nucleic acid of the plant is brought into contact with a labeled probe comprising at least 10 nucleotides of the orf 522 sequence.

Other variants and characteristics of the invention will become clear by reading the examples which follow:

EXAMPLE 1

Preparation of the Plant Material

Seeds of *Cichorium intybus* L. cv. Pévèle were provided by Florimond Desprez, and (cytoplasmic male-sterility, or SMC) *Helianthus annuus* seeds were obtained commercially.

The *Cichorium intybus* seeds were surfaced-sterilized with a 0.1% (w/v) $HgCl_2$ solution, washed three times with distilled water and placed into Petri dishes on Heller's culture medium (1953) (macro- and microsalts, without $FeCl_3$) supplemented with 19.5 mg/l Fe-EDTA; 20 g/l sucrose and 6 g/l agar (Bioakar type E) and cultivated under the culture conditions described by Rambaud et al (1990). The aseptic seedlings were then transferred onto the same medium in culture tubes. The *Helianthus annuus* seeds were sterilized with a 50 g/l calcium hypochlorite solution and then washed three times with distilled water and transferred into a solution of sucrose (10 g/l)/agar (0.6%).

Chicory leaves were harvested from 12- to 14-day old plants. The leaves were cut into pieces and incubated in a solution with 15 g/l caylase 345, 0.5 g/l caylase M2 (Cayla, Toulouse, France) and 90 g/l mannitol.

As far as the sunflower seeds are concerned, the hypocotyls were removed 6 to 10 days after germination and incubated in the same maceration solution.

The protoplasts were incubated for 5 hours and 30 minutes at 30° C. in the dark without moving, purified by filtration through 50 μm-mesh sieves, harvested and washed three times by low-speed centrifugation (100×g) for 15 min.

After the supernatant had been removed using a Pasteur pipette, the protoplasts were mixed in a ratio of 1:3 (sunflower/chicory) to obtain a suspension comprising from 7 to 11.106 protoplasts/ml.

The protoplasts were fused by the method of Kao (Wetter LRL and Constabel F (eds) Plant Tissue Culture Methods, ch 7, pp 49–56, 1982), with the following modifications: one volume of a solution of protoplast mixture was placed into a Petri dish, and three volumes of a solution of 30% polyethylene glycol (PEG 4000 Serva) with 10% dimethyl sulfoxide (DMSO) were added dropwise. After gentle homogenization, the solution was left to rest for three minutes. One minute later, another 3.5 volumes of Kao's solution number 3 (1982) are added. Then, 3.5 volumes of Kao's solution number 3 (1982) are added, and 3 minutes later 6×3.5 volumes of washing medium (Saksi N et al. CR Acad. Sci. Paris 302: 165–170, 1986) are added. The protoplasts are harvested by centrifugation (8 min, 100×g) after 10–15 minutes; they are then washed 3 times with 8 ml aliquots of the washing medium and resuspended in MCl culture medium (Saksi et al, 1986), in which the concentration of 1-naphthylacetic acid (NAA) is 2 mg/l, the inositol concentration is 250 mg/l and the $KNO_3$ concentration is 144 mg/l.

After one or two days of culture in this medium to a density of $2.10^4$ protoplasts/ml, the heterokaryocytes isolated are cultured at low density (12/100 μl) at 30° C. in a modified MCl medium (0.5 mg/l NAA) to which are added 2-(N-morpholino)ethanesulfonic acid (MES) (5 mM), casein hydrolysate (150 mg/l) and coconut milk (2%; v/v).

One month later, the colonies obtained from the fusions of heteroplasmic protoplasts are transferred to a proliferation medium and then onto a regeneration medium (Rambaud et al. 1990). After rooting, the plants were transferred to the greenhouse for several weeks and then transplanted into the field.

The plants obtained have a chicory phenotype. Amongst them, the line designated CT 52/3 shows male sterility by lack of anther dehiscence; line CT 41/1 shows male sterility by the complete absence of anthers.

EXAMPLE 2

Materials and Methods

Plant Material

Sixteen populations of industrial chicories with normal cytoplasm numbered FD1 to FD16, the industrial chicory cv. Pévèle, and a family of industrial chicory (CT 41/1) 20540 U with male cytoplasmic sterility (cms) provided by the company Florimond-Desprez, a chicory CT 52/3 (cms), the sunflower cv. Mirasol (cms). The young leaves were removed from greenhouse-grown plants and stored at −80° C.

DNA

Adaptation of the protocols of the Dellaporta-laboratory (Plant. Mol. Report., 1983) for total DNA miniextraction: the steps were carried out at 4° C. Finely grind with liquid nitrogen a leaf section of 150 to 200 mg fresh weight. Transfer into a 2 ml microtube. Add 940 μl of buffer solution Tris-HCl 0.1 M pH 8.0, EDTA 50 mM, NaCl 0.5 M, β-mercaptoethanol 10 mM. Add 62 μl of 20% SDS and vortex vigorously. Incubate for 15 minutes at 65° C. Add 310 μl of 5 M potassium acetate and vortex vigorously. Leave to precipitate for 30 minutes. Centrifuge. Centrifuge for 15 minutes at 17,500 g. Transfer 1 ml of the supernatant into a 2 ml microtube. Add 0.5 ml of isopropanol and mix. Leave to precipitate for 15 minutes. Centrifuge for 10 minutes at 12,000 g. Decant the supernatant using a micropipette. Dry the pellets in a Speed-Vac apparatus for 10 minutes at a low temperature setting. Redissolve the pellets in 100 μl of buffer solution Tris-HCl 50 mM pH 8.0, EDTA 10 mM, ribonuclease A 0.2 mg/ml and incubate for 2 hours at 37° C. Extract three times with phenol and then once with chloroform. Add 0.1 volume of 3 M sodium acetate pH 5.2 and two volumes of absolute ethanol at 4° C. Leave to precipitate for 15 minutes at 4° C. Centrifuge for 10 minutes at 12,000 g. Wash the pellet wish 70% ethanol at 4° C. Centrifuge for 3 minutes at 12,000 g. Decant using a micropipette and dry for 10 minutes in the Speed-Vac at low temperature. Take up the pellet in a buffer solution of Tris/HCl 1 mM ph 8.0, EDTA 0.1 mM.

Quantify a 5 μl aliquot by horizontal electrophoresis in 08% agarose gel, TBE ix, EtBr 0.5 μg/ml.

PCR

Two primers of 23 and 26 bases which flank a 347 bp fragment within the orf 522 sequence (Köhler et al., Mol. Gen. Genet., 1991). Primer sequences:

SEQ ID NO 1: 5'CCCCCTCCCTGGTGGATCCGGCG3'

SEQ ID NO 2: 5'CCCTCTATGAGTACCGTTCTCT-CACG3'

The 60 Bio-Med thermocycler is programed as follows: first cycle: 3 min, 92° C.; 30 cycles: 1.30s, 92° C.; 2.30s, 55° C.; 3.1 min, 72° C.; last cycle: 5 min, 72° C. Reaction mixture: Appligène buffer 1x: Tris-HCl 10 mM pH 9.0. Triton X-100 0.1%, $MgCl_2$ 1.5 mM, BSA 0.2 mg/ml; dNTP 100 μM; primers 0.2 μM each; Appligène Taq polymerase 2 U/100 μl ; DNA matrix 50 ng/100 μl; H₂O to 10 μl; mineral oil: 50 μl. Analysis of the products by horizontal electrophoresis in 1.6% agarose gel, TBE 1×, EtBr 0.5 μg/ml.

Hybridizations

Traditional transfer technique by the Southern method ("Maniatis"). Chemical labeling of the orf 522 probe using the Dig-High-Prime kit (Böehringer-Mannheim). Visualization as described in the Böehringer-Mannheim protocol using CSPD (Tropix) as chemoluminescent substrate. Exposure time of the membranes: from one hour to one night in the case of very weakly amplified fragments Results The total DNA of 4 individuals per population FD1 to FD16, 8 individuals of the family 20540 U, of chicory CT 52/3 and of sunflower "Mirasol" were extracted, that is a total of 73 individuals. Absence of inhibition of the PCR by impurities present in the DNA extracts was checked by adding several tens of femtograms of the 347 bp fragment to each reaction mixture. All the PCR analyses of the 52/3 DNA, sunflower "Mirasol" DNA and the DNA of the family 20540 U allow amplification of a substantial quantity (approx. 200 ng) of the approx. 350 bp fragment of orf 522. All the chicories with a normal cytoplasm lack this fragment. Analysis of these PCR products by molecular hybridization with the aid of an or 522 probe prepared by PCR from total DNA of Mirasol sunflower confirms the homology between the amplified fragment in the (cms) chicories and the probe.

Conclusion

The results obtained have demonstrated that orf 522 is not present in fertile chicories. The determination by means of PCR of the presence/absence of the orf 522 sequence can therefore be considered for routine analysis.

What is claimed is:

1. A method of producing a chicory plant that exhibits cytoplasmic male sterility comprising:

(a) introducing into cells of a chicory plant a mitochondrion of a male sterile plant that comprises the orf 522 sequence of *Helianthus annuus;*

(b) regenerating chicory plants; and (c) identifying a chicory plant comprising a 347 bp fragment of said orf 522 comprising the nucleotide sentences of SEQ ID NO: 1 and SEQ ID NO: 2.

2. The method of claim 1, wherein the chicory plant comprises a nucleus from *Cichorium intybus* or *Cichorium endivia*.

3. The method of claim 1, further comprising crossing the chicory plant as the female parent with a second chicory plant.

4. The method of claim 3, wherein the second chicory plant does not exhibit cytoplasmic male sterility.

5. A method of producing a chicory plant cell that expresses cytoplasmic male sterility comprising:
(a) fusing chicory plant cells with cells of a second plant cell that comprises a nucleotide sequence conferring cytoplasmic male sterility, wherein the nucleotide sequence comprises a 347 bp fragment of the orf 522 of *Helianthus annuus* comprising the nucleotide sequences of SEQ ID NO: 1 and SEQ ID NO: 2; and
(b) detecting the 347 bp fragment in the plant cells.

6. The method of claim 5, wherein the chicory plant cells are from *Cichorium intybus* or *Cichorium endivia*.

7. The method of claim 5, wherein the second plant cell is from *Helianthus annuus*.

8. The method of claim 5, further comprising regenerating a chicory plant having cytoplasmic male sterility from a fused chicory plant cell comprising the 347 bp fragment.

9. The method of claim 8, further comprising crossing the regenerated chicory plant as the female parent with a second chicory plant.

10. The method of claim 9, wherein the second plant does not exhibit cytoplasmic male sterility.

\* \* \* \* \*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:1:

CCCCCTCCCT GGTGGATCCG GCG        23

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:2:

CCCTCTATGA GTACCGTTCT CTCACG        26